(12) United States Patent
Fein et al.

(10) Patent No.: US 12,059,189 B2
(45) Date of Patent: Aug. 13, 2024

(54) COMPRESSION/REDUCTION DRIVERS FOR PERFORMING SURGICAL METHODS

(71) Applicant: ARTHREX, INC., Naples, FL (US)

(72) Inventors: Paul Fein, Maynard, MA (US); Thomas Anstead, Naples, FL (US)

(73) Assignee: ARTHREX, INC., Naples, FL (US)

( * ) Notice: Subject to any disclaimer, the term of this patent is extended or adjusted under 35 U.S.C. 154(b) by 228 days.

(21) Appl. No.: 17/348,143

(22) Filed: Jun. 15, 2021

(65) Prior Publication Data
US 2021/0393307 A1   Dec. 23, 2021

Related U.S. Application Data

(60) Provisional application No. 63/040,240, filed on Jun. 17, 2020.

(51) Int. Cl.
| | |
|---|---|
| A61B 17/88 | (2006.01) |
| A61B 17/56 | (2006.01) |
| A61B 17/68 | (2006.01) |
| A61B 17/86 | (2006.01) |

(52) U.S. Cl.
CPC ...... A61B 17/8875 (2013.01); A61B 17/8866 (2013.01); *A61B 2017/564* (2013.01); *A61B 2017/681* (2013.01); *A61B 17/8645* (2013.01)

(58) Field of Classification Search
CPC .............. A61B 2017/681; A61B 17/88; A61B 17/8872; A61B 17/8875; A61B 17/888; A61B 17/8886; A61B 17/8891; A61B 17/8645; A61B 17/8877; B25B 15/04; B25B 15/06
See application file for complete search history.

(56) References Cited

U.S. PATENT DOCUMENTS

| | | | | |
|---|---|---|---|---|
| 2,845,968 A * | 8/1958 | Luber | ................ | B25B 23/10 81/451 |
| 5,101,697 A * | 4/1992 | Fishback | ................ | B25B 23/045 81/433 |
| 5,341,708 A * | 8/1994 | Nick | ................ | B25B 23/10 81/429 |
| 6,668,941 B2 * | 12/2003 | Phillips | ................ | B25B 23/005 173/4 |
| 6,845,693 B1 * | 1/2005 | Babij, Jr. | ................ | B25B 23/04 81/57.37 |
| 7,089,829 B2 * | 8/2006 | Chen | ................ | B25B 23/0035 81/62 |
| 7,141,074 B2 * | 11/2006 | Fanger | ................ | A61B 17/1757 606/80 |

(Continued)

FOREIGN PATENT DOCUMENTS

KR   10-1573774   12/2015

*Primary Examiner* — Larry E Waggle, Jr.
(74) *Attorney, Agent, or Firm* — Carlson, Gaskey & Olds, P.C.

(57) ABSTRACT

Compression/reduction drivers for performing surgical methods are provided. Exemplary surgical methods that may be performed using the compression/reduction drivers described herein include, but are not limited to, arthrodesis procedures (i.e., bone fusion procedures), fracture fixation procedures, etc. The compression/reduction drivers are configured to simultaneously and independently apply a force against a bone segment and drive a fixation device into the bone segment.

19 Claims, 8 Drawing Sheets

(56) References Cited

U.S. PATENT DOCUMENTS

| | | | |
|---|---|---|---|
| 7,147,641 B2 | 12/2006 | Chen | |
| 7,290,465 B2 * | 11/2007 | Gao | B25B 15/04 |
| | | | 81/62 |
| 7,291,104 B2 | 11/2007 | Neisz et al. | |
| 7,487,699 B2 * | 2/2009 | Xu | B25B 23/10 |
| | | | 81/434 |
| 7,572,264 B2 | 8/2009 | Null et al. | |
| 8,052,691 B2 | 11/2011 | Zwirnmann et al. | |
| 8,377,065 B2 * | 2/2013 | Kuntz | A61B 17/7076 |
| | | | 606/86 A |
| 8,425,521 B2 | 4/2013 | Cremer et al. | |
| 8,459,155 B2 | 6/2013 | Canizares, Jr. et al. | |
| 9,186,138 B2 | 11/2015 | Corradi et al. | |
| 10,188,387 B2 | 1/2019 | Sniffin et al. | |
| 10,307,153 B2 * | 6/2019 | Nordmeyer | A61B 17/8894 |
| 10,405,897 B2 | 9/2019 | Beretta et al. | |
| 10,531,903 B2 | 1/2020 | Daly et al. | |
| 2006/0025773 A1 | 2/2006 | Yevmenenko et al. | |
| 2008/0041196 A1 | 2/2008 | Companioni et al. | |
| 2019/0192206 A1 * | 6/2019 | Rippe | B25B 23/101 |
| 2019/0269421 A1 * | 9/2019 | Nino | A61B 17/1695 |
| 2020/0188004 A1 * | 6/2020 | Flores | A61B 17/8886 |
| 2021/0045754 A1 * | 2/2021 | Khosla | A61B 90/03 |

\* cited by examiner

FIG. 10

COMPRESSION/REDUCTION DRIVERS FOR PERFORMING SURGICAL METHODS

CROSS-REFERENCE TO RELATED APPLICATIONS

This disclosure claims priority to U.S. Provisional Application No. 63/040,240, filed on Jun. 17, 2020, the entire disclosure of which is incorporated herein by reference.

BACKGROUND

This disclosure relates to the field of surgery, and more particularly to compression/reduction drivers for use during various surgical methods.

Some surgical procedures require installing compression screws or other fixation devices across multiple bones or bone fragments in order to stabilize the bones/bone fragments relative to one another. Depending on the anatomy, surgeons may have difficulty achieving adequate compression across a gap between the bones/bone fragments while inserting the fixation devices due to challenges associated with maintaining reduction of the bones/bone fragments.

SUMMARY

This disclosure is directed to compression/reduction drivers for performing surgical procedures, such as arthrodesis procedures (i.e., bone fusion procedures), bone fracture fixation procedures, or osteotomy procedures, for example.

An exemplary compression/reduction driver may include, inter alia, a handle, a drive shaft removably or permanently secured to the handle, a spring retaining sleeve secured to the drive shaft, a compression sleeve movably secured to the spring retaining sleeve, and a spring extending between a first bearing surface of the spring retaining sleeve and a second bearing surface of the compression sleeve. The handle is rotatable relative to the drive shaft to apply a rotational driving force to the drive shaft, and the spring is configured to apply a biasing force to bias the compression sleeve distally in a direction away from the spring retaining sleeve.

An exemplary surgical method may include, inter alia, during insertion of a fixation device into a first bone segment and a second bone segment, simultaneously (a) applying a force against the first bone segment with a compression sleeve of a compression/reduction driver, and (b) driving the fixation device into the first bone segment and the second bone segment with a drive shaft of the compression/reduction driver.

DETAILED DESCRIPTION

This disclosure is directed to compression/reduction drivers for performing surgical methods. Exemplary surgical methods that may be performed using the compression/reduction drivers described herein include, but are not limited to, arthrodesis procedures (i.e., bone fusion procedures), fracture fixation procedures, etc. These and other features of this disclosure are described in further detail below.

An exemplary compression/reduction driver may include, inter alia, a handle, a drive shaft removably secured to the handle, a spring retaining sleeve secured to the drive shaft, a compression sleeve movably secured to the spring retaining sleeve, and a spring extending between a first bearing surface of the spring retaining sleeve and a second bearing surface of the compression sleeve. The handle is rotatable relative to the drive shaft to apply a rotational driving force to the drive shaft, and the spring is configured to apply a biasing force to bias the compression sleeve distally in a direction away from the spring retaining sleeve.

In a further embodiment, a handle of a compression/reduction driver is a ratcheting handle that includes a gripping portion and a toggle that is rotatable relative to the gripping portion to control a direction of a rotational driving force of a drive shaft.

In a further embodiment, a handle of a compression/reduction driver includes a release button depressible for releasing a drive shaft from the handle.

In a further embodiment, a drive shaft of a compression/reduction driver includes an engagement feature configured to engage a fixation device.

In a further embodiment, an engagement feature of a drive shaft of a compression/reduction driver is adapted to engage a headless compression screw, and the engagement feature is a hexalobular or star-shaped driver tip.

In a further embodiment, a spring retaining sleeve of a compression/reduction driver includes a first slot through which a spring and a drive shaft are visible, and a compression sleeve of the compression/reduction driver includes a second slot through which the drive shaft is visible.

In a further embodiment, a spring retaining sleeve of a compression/reduction driver includes an internal thread that engages a threaded portion of a drive shaft.

In a further embodiment, a spring retaining sleeve of a compression/reduction driver is secured to a drive shaft by a weld or a bonding agent.

In a further embodiment, a compression sleeve of a compression/reduction driver is movably secured to a spring retaining sleeve by a bayonet mount.

In a further embodiment, a bayonet mount of a compression/reduction driver includes a pin on a compression sleeve and an L-shaped slot on a spring retaining sleeve.

In a further embodiment, a distal end portion of a compression sleeve of a compression/reduction driver includes a bone engaging surface.

In a further embodiment, a bone engaging surface of a compression sleeve includes a plurality of bone engaging teeth at a serrated surface.

In a further embodiment, a pair of fixation device gripping legs are operably coupled to a spring or a drive shaft of a compression/reduction driver.

An exemplary surgical method may include, inter alia, during insertion of a fixation device into a first bone segment and a second bone segment, simultaneously (a) applying a force against the first bone segment with a compression sleeve of a compression/reduction driver, and (b) driving the fixation device into the first bone segment and the second bone segment with a drive shaft of the compression/reduction driver.

In a further embodiment, a fixation device inserted during a surgical method is a headless compression screw.

In a further embodiment, applying a force against a first bone segment during a surgical method includes biasing a bone engaging surface of a compression sleeve of a compression/reduction driver against an exterior surface of the first bone segment.

In a further embodiment, a force exerted against a first bone segment during a surgical method reduces a gap between the first bone segment and a second bone segment prior to a fixation device engaging the second bone segment.

In a further embodiment, prior to applying a force to a bone segment or driving a fixation device into a bone segment, a surgical method includes preparing a first pilot hole in a first bone segment, and preparing a second pilot hole in a second bone segment.

In a further embodiment, a first bone segment and a second bone segment are bone fragments of a fractured bone.

In a further embodiment, a first bone segment and a second bone segment are separate bones.

Figure 1:
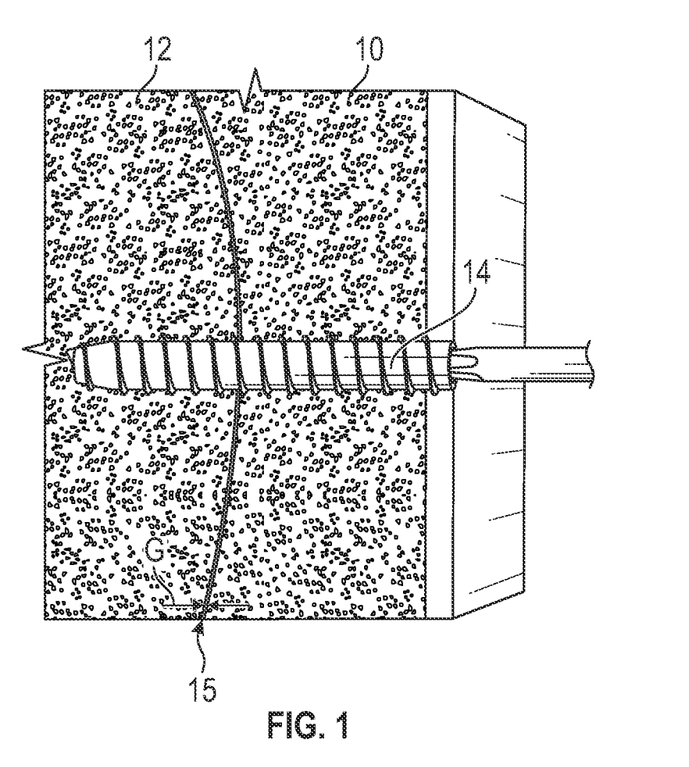
FIG. 1 illustrates bone segments of a human musculoskeletal system.

FIG. 1 schematically illustrates select portions of the human musculoskeletal system. A first bone segment 10 and a second bone segment 12 of the human musculoskeletal system are specifically shown. The first bone segment 10 and the second bone segment 12 may be separate bones of the human musculoskeletal system or could be bone fragments associated with a single bone. The first and second bone segments 10, 12 could be part of a foot, ankle, hand, wrist, etc.

Many surgical procedures require installing a fixation device 14 (e.g., a compression screw) across the first and second bone segments 10, 12 in order to stabilize the first and second bone segments 10, 12 relative to one another. A surgeon may experience difficulty achieving adequate compression across a fracture line/arthrodesis site 15 between the first and second bone segments 10, 12 while inserting the fixation device 14. For example, the fixation device 14 may not adequately reduce a gap G that extends between the first and second bone segments 10, 12. Exemplary compression/reduction drivers capable of simultaneously maintaining reduction of the first and second bone segments 10, 12 and driving the fixation device 14 through the first and second bone segments 10, 12 are therefore detailed herein.

Figure 2:
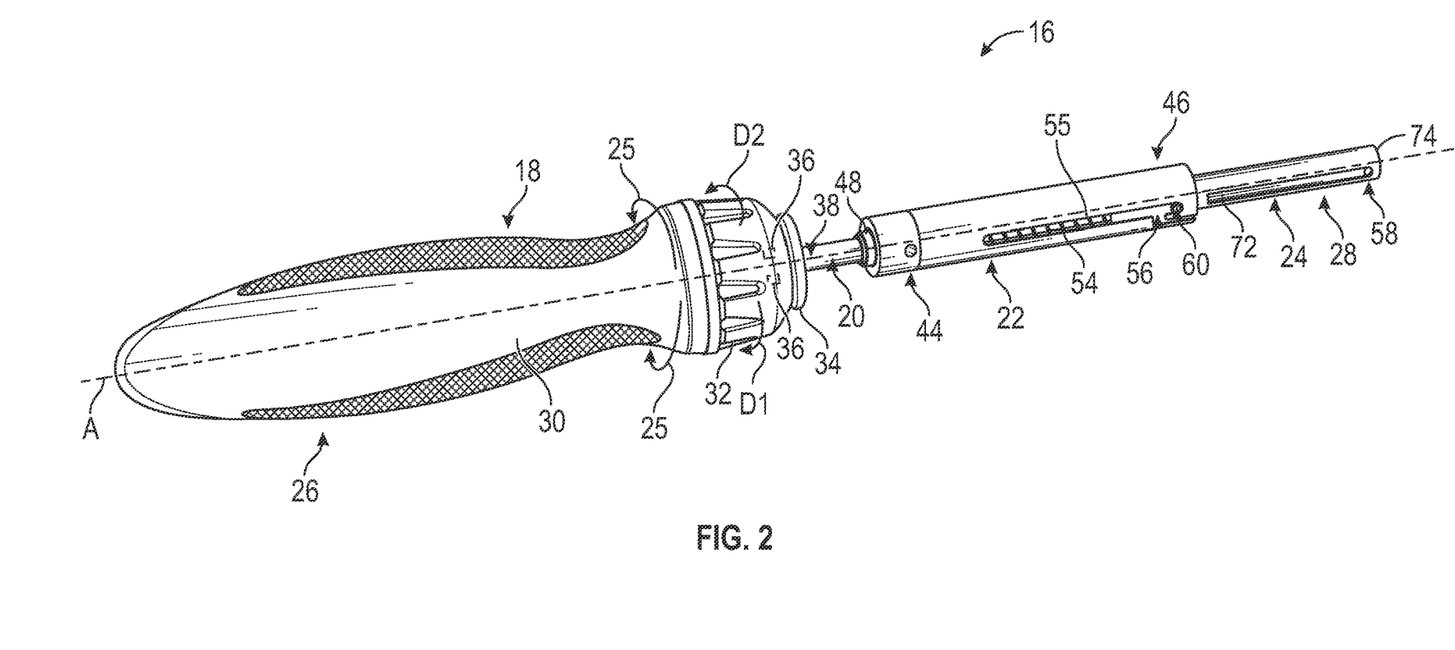
FIG. 2 is a perspective view of an exemplary compression/reduction driver for use during surgical procedures.
Figure 3:
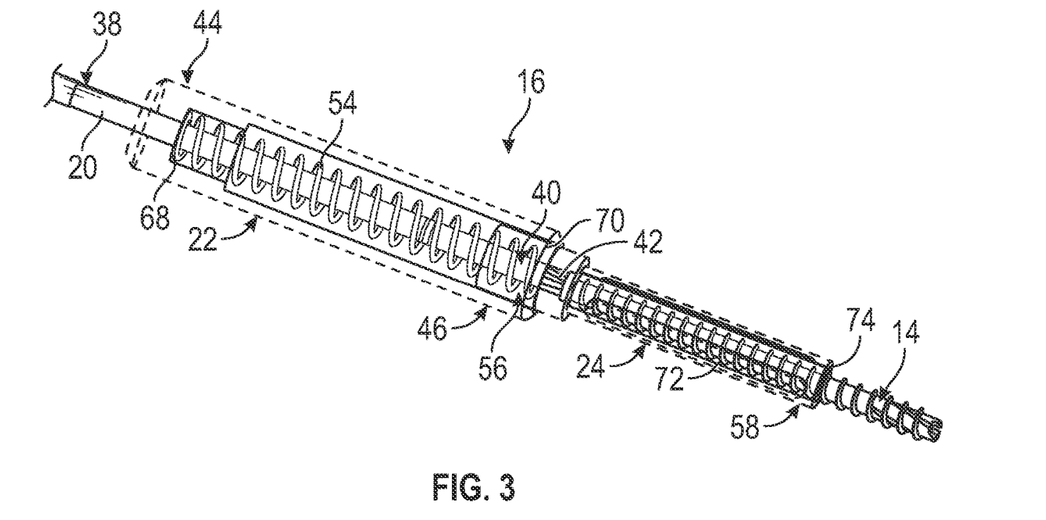
FIG. 3 illustrates a relaxed position of the compression/reduction driver of FIG. 2.
Figure 4:
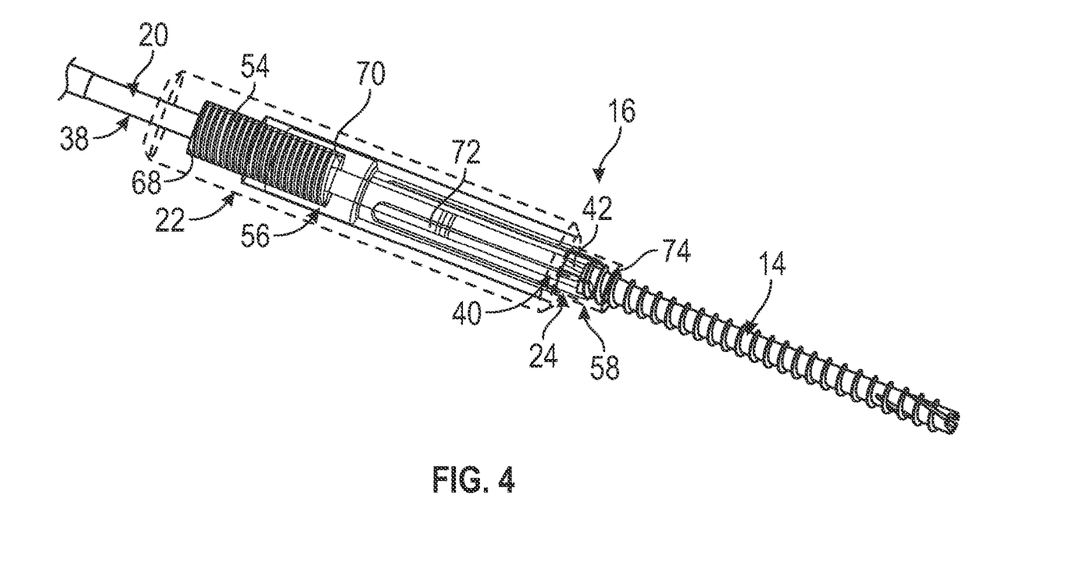
FIG. 4 illustrates a retracted position of the compression/reduction driver of FIG. 2.

FIGS. 2-4 illustrate an exemplary compression/reduction driver 16 for use during various surgical methods. As discussed in greater detail below, the compression/reduction driver 16 is configured to provide force/reductive assistance against bone segments during insertion of a fixation device through the bone segments. Advantageously, the force/reductive assistance may be provided independent from the force applied to the bone segments by the fixation device 14 during the insertion. The force/reductive assistance may further be provided independent of the torque/force required to install the fixation device 14.

The compression/reduction driver 16 may include a handle 18 (see FIG. 2), a drive shaft 20, a spring retaining sleeve 22, and a compression sleeve 24. The compression/reduction driver 16 extends along a longitudinal axis A between a first or proximal portion 26 and a second or distal portion 28. The handle 18 is disposed at the proximal portion 26 of the compression/reduction driver 16, and the compression sleeve 24 is disposed at the distal portion 28 of the compression/reduction driver 16. The overall dimensions of the compression/reduction driver 16 are not intended to limit this disclosure.

The handle 18 may be selectively rotated relative to the drive shaft 20 by twisting the handle 18 circumferentially about the longitudinal axis A, which is schematically shown by arrows 25 in FIG. 2. Rotation of the handle 18 may rotate the drive shaft 20 about the longitudinal axis A for applying a rotational driving force to the fixation device 14. In an embodiment, the handle 18 is a ratcheting handle. Thus, in some embodiments, the handle 18 can be rotated relative to the drive shaft 20 without also turning the drive shaft 20 in either an advancing direction or a retracting direction.

The handle 18 of the compression/reduction driver 16 may include a gripping portion 30, a toggle 32, and a release button 34. The gripping portion 30 may be ergonomically gripped and held by a surgeon during use of the compression/reduction driver 16.

The toggle 32 may be actuated relative to the gripping portion 30 in order to configure the drive shaft 20 for applying the rotational driving force for either advancing or retracting the fixation device 14. For example, the toggle 32 may be rotated in a first direction D1 to configure the drive shaft 20 for advancing the fixation device 14 or may be rotated in a second direction D2 to configure the drive shaft 20 for retracting the fixation device 14.

The release button 34 is configured for releasing the drive shaft 20 from the gripping portion 30 of the handle 18. For example, the release button 34 may be depressed in a direction toward the toggle 32 in order to remove the drive shaft 20 from the gripping portion 30. Depressing the release button 34 may displace one or more bearings 36 located inside the release button 34 from one or more detents formed in a proximal end portion 38 of the drive shaft 20, thereby permitting removal of the drive shaft 20 from the gripping portion 30.

The drive shaft 20 extends along the longitudinal axis A between the proximal end portion 38 and a distal end portion 40. The distal end portion 40 of the drive shaft 20 may include an engagement feature 42 (best shown in FIGS. 3 and 4) that is configured to engage a corresponding engagement feature of the fixation device 14. In an embodiment, the engagement features 42 is a hexalobular or star-shaped driver tip. However, other configurations for the engagement feature 42 are also contemplated within the scope of this disclosure.

In an embodiment, the fixation device 14 is a compression screw. In another embodiment, the fixation device 14 is a headless compression screw, such as a Compression FT Screw sold by Arthrex, Inc. However, other fixation devices may also be utilized in combination with the compression/reduction driver 16 within the scope of this disclosure.

The drive shaft 20, the spring retaining sleeve 22, and the compression sleeve 24 are coaxial relative to one another, and at least a portion of the drive shaft 20 may be circumscribed by each of the spring retaining sleeve 22 and the compression sleeve 24. The drive shaft 20 extends entirely through the spring retaining sleeve 22 and may extend at least partially through the compression sleeve 24. In a relaxed state of the compression/reduction driver 16 (see FIG. 3), the engagement feature 42 of the drive shaft 20 extends a slight distance beyond the spring retaining sleeve 22 and into the compression sleeve 24. In an embodiment, the engagement feature 42 extends a distance into the compression sleeve 24 that is less than 50% of the overall length of the compression sleeve 24 in the relaxed state of the compression/reduction driver 16. In another embodiment, the engagement feature 42 extends a distance into the compression sleeve 24 that is less than 25% of the overall length of the compression sleeve 24 in the relaxed state of the compression/reduction driver 16.

Figure 5:
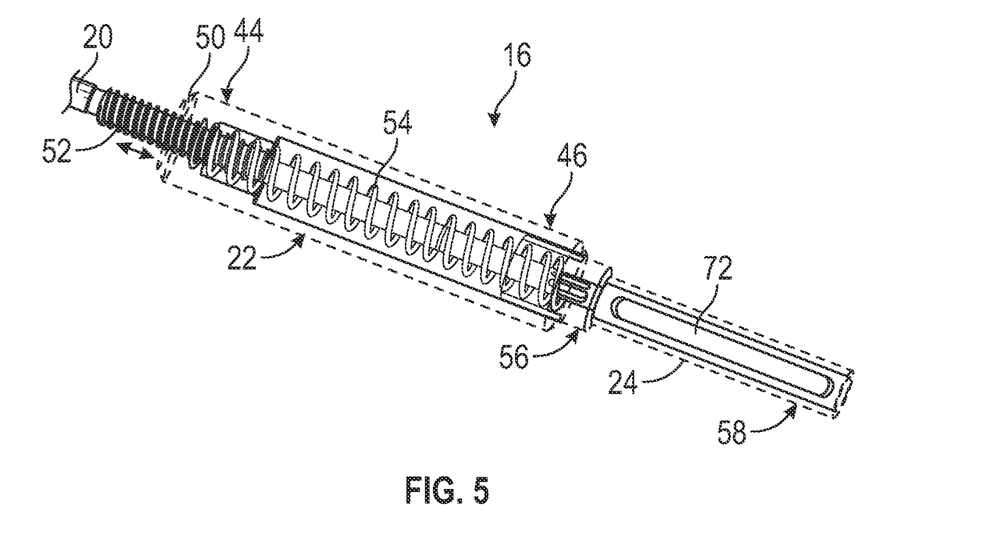
FIG. 5 illustrates a threaded connection between a drive shaft and a spring retaining sleeve of a compression/reduction driver.

The spring retaining sleeve 22 includes a cylindrical body that extends between a proximal end portion 44 and a distal end portion 46. The proximal end portion 44 of the spring retaining sleeve 22 may be fixedly secured to the drive shaft 20. In an embodiment, the spring retaining sleeve 22 is secured to the drive shaft 20 by a weld or bonding agent 48 (see FIG. 2). In another embodiment, the spring retaining sleeve 22 includes an internal thread 50 that is configured to mate with a threaded portion 52 of the drive shaft 20 (see FIG. 5). In this way, a surgeon may adjust the length of the drive shaft 20 that extends into the compression sleeve 24, thereby controlling the amount of force distributed by the compression/reduction driver 16 during its use and reducing the amount of force necessary to re-engage the fixation device 14 during its insertion. This feature may further expand the range of available fixation devices that can be engaged by the compression/reduction driver 16.

A spring 54 may be received over the drive shaft 20 and may be substantially housed within the spring retaining sleeve 22. In an embodiment, the spring 54 is a coil spring. However, other springs may also be suitable and are further contemplated within the scope of this disclosure. As discussed in greater detail below, the spring 54 is configured to apply a biasing force against the compression sleeve 24 in order to bias the compression sleeve 24 into contact with a bone segment when inserting the fixation device 14 via the compression/reduction driver 16. Portions of the spring 54 and the drive shaft 20 may be visible through an elongated slot 55 formed in the spring retaining sleeve 22.

The compression sleeve 24 may include a tapered cylindrical body that extends between a proximal end portion 56 and a distal end portion 58. The proximal end portion 56 may include a first diameter that is larger than a second diameter of the distal end portion 58 but smaller than a third diameter of the distal end portion 46 of the spring retaining sleeve 22. Therefore, the compression sleeve 24 may translate in both the proximal and distal directions relative to the drive shaft 20 and the spring retaining sleeve 22.

Figure 6:
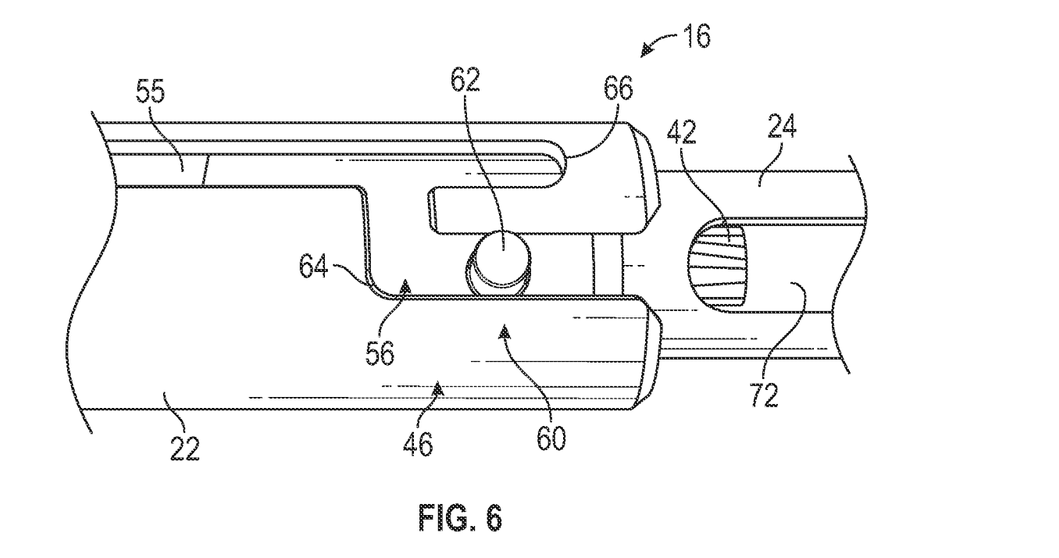
FIG. 6 illustrates a connection between a compression sleeve and a spring retaining sleeve of a compression/reduction driver.

The compression sleeve 24 may be removably attached to the spring retaining sleeve 22. In an embodiment, the compression sleeve 24 is removably connected to the spring retaining sleeve 22 by a bayonet mount 60. For example, as best shown in FIGS. 2 and 6, the proximal end portion 56 of the compression sleeve 24 may include a pin 62 that may be received within an L-shaped slot 64 formed in the distal end portion 46 of the spring retaining sleeve 22. The L-shaped slot 64 opens into the elongated slot 55 of the spring retaining sleeve 22. The pin 62 may be received against a distal surface 66 of the elongated slot 55 to couple the compression sleeve 24 to the spring retaining sleeve 22. The pin 62 may be moved from the elongated slot 55 through the L-shaped slot 64 to disconnect the compression sleeve 24 from the spring retaining sleeve 22.

As best shown in FIGS. 3-4, when the compression sleeve 24 is assembled to the spring retaining sleeve 22, the spring 54 may extend between a first bearing surface 68 provided by an inner surface of the proximal end portion 44 of the spring retaining sleeve 22 and a second bearing surface 70 provided by an inner surface of the proximal end portion 56 of the compression sleeve 24. The spring 54 applies a biasing force against the second bearing surface 70 to bias the compression sleeve 24 distally. The compression sleeve 24 may be translated between the relaxed position shown in FIG. 3 and the retracted position shown in FIG. 4, or any position therebetween, by moving the compression sleeve 24 proximally in order to compress the spring 54.

One or more elongated slots 72 may be formed in the compression sleeve 24. In an embodiment, two elongated slots 72 are provided at opposing sides of the compression sleeve 24. The elongated slots 72 function as windows for visualizing portions of the drive shaft 20 and the fixation device 14 during use of the compression/reduction driver 16. For example, a surgeon may observe the progress of the fixation device 14 during implantation via the elongated slot 72.

Figure 7:
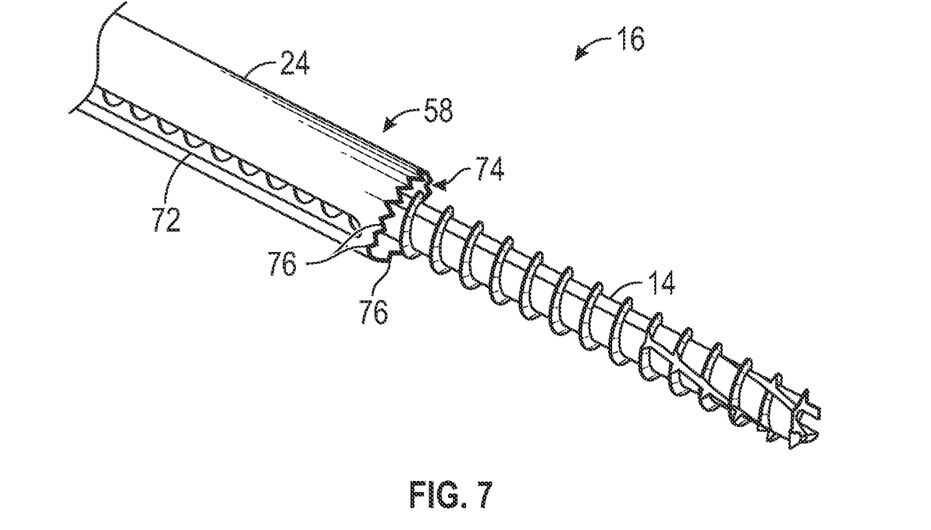
FIG. 7 illustrates an exemplary bone engaging surface of a compression sleeve of a compression/reduction driver.

The distal end portion 58 of the compression sleeve 24 may include a bone engaging surface 74. In an embodiment, the bone engaging surface 74 is a smooth surface (see FIGS. 2-4). In another embodiment, the bone engaging surface 74 is a serrated surface having a plurality of bone-engaging teeth 76 (see FIG. 7). During use of the compression/reduction driver 16, the spring 54 biases the bone engaging surface 74 into engagement with a bone segment, thereby applying a force against the bone segment. The force applied to the bone segment by the bone engaging surface 74 therefore provides reduction assistance that is independent of the force applied by the fixation device 14 during its insertion.

Figure 8A:
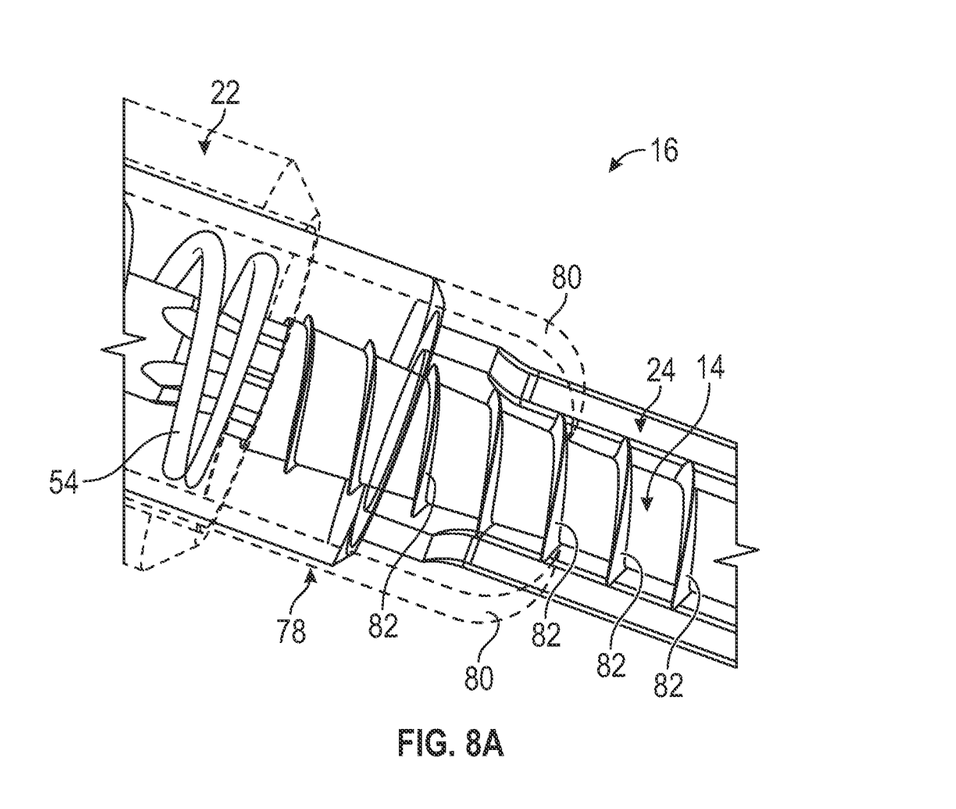
FIGS. 8A, 8B, and 8C illustrate fixation device retaining features of a compression/reduction driver.

Referring now primarily to FIG. 8A, the compression/reduction driver 16 may additionally include a retaining feature 78 that is configured to interface with the fixation device 14 during use of the compression/reduction driver 16. The retaining feature 78 may include a pair of gripping legs 80 that may be operably connected to either the spring 54 or the drive shaft 20. The gripping legs 80 may extend through portions of the compression sleeve 24 for selectively engaging threads 82 of the fixation device 14.

The spring 54 (or the drive shaft 20) may control the position of the gripping legs 80 relative to the fixation device 14. For example, when a user pushers the handle 18 of the compression/reduction driver 16 distally, the gripping legs 80 may retract from the threads 82 to allow the fixation device 14 to pass in the distal direction. Furthermore, when the handle 18 of the compression/reduction driver 16 is unloaded such that the handle 18 begins to move proximally, the gripping legs 80 may engage distal-facing surfaces of the threads 82 in order to maintain a positioning of the compression sleeve 24 relative to the spring retaining sleeve 22. The retaining feature 78 therefore substantially eliminates the need for the user to re-engage the fixation device 14 each time force is released on the handle 18 of the compression/reduction driver 16.

Figure 8B:
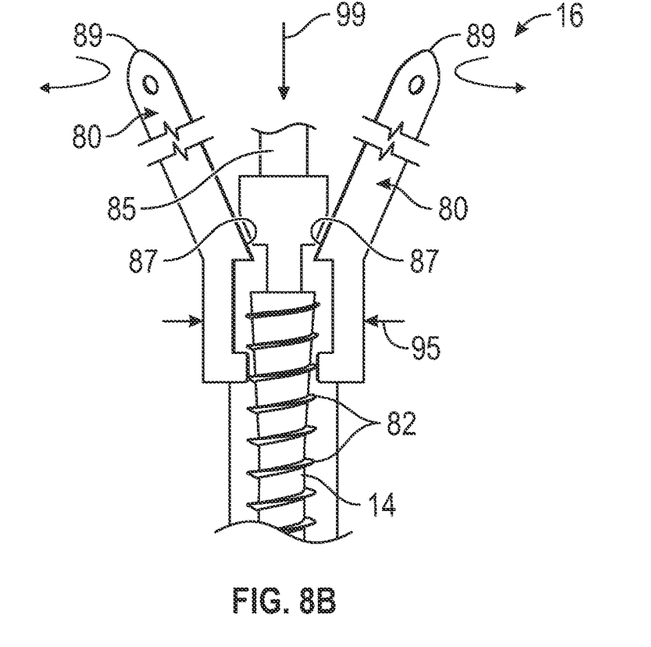
Figure 8C:
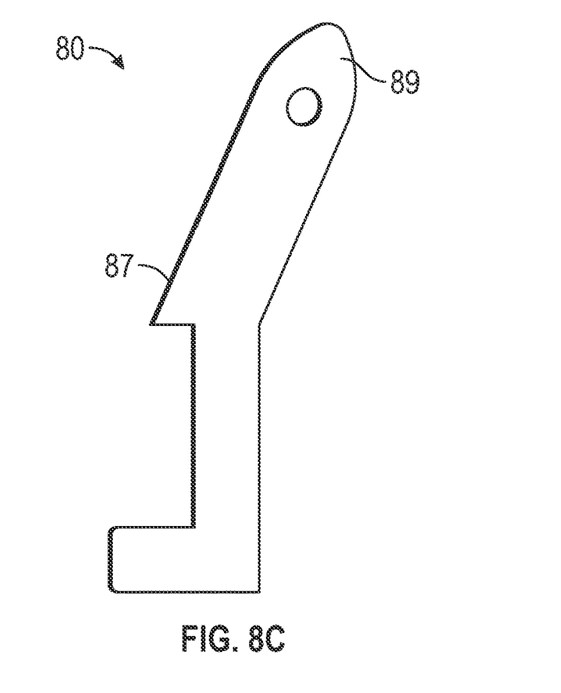

Referring now primarily to FIGS. 8B and 8C, the gripping legs 80 may be actively engaged by an inward pressing force 99 (e.g., generated by a spring or some other force generating component), thereby pushing the gripping legs 80 away from the fixation device 14. A mating engagement feature 85 of either the drive shaft 20 or the compression sleeve 24 may engage a sloped wall 87 of the gripping legs 80 during the downward motion of either the drive shaft 20 or the compression sleeve 24 in order to rotate the gripping legs 80 away from the fixation device 14. The gripping legs 80 may be made of steel or some other similar material with a matching thread form, or from a malleable surface such as a plastic, or having a negative shape of a single thread form. The gripping legs 80 may include a hinge point 89 that controls their rotation. The gripping legs 80 may be biased in a direction toward the fixation device 14 by an inward pressing force 95 when the inward pressing force 99 is not being applied.

FIGS. 9-12, with continued reference to FIGS. 1-8, schematically illustrate, in sequential order, an exemplary surgical method for performing an arthrodesis procedure or a fracture procedure, for example. In an embodiment, the surgical method is a subtalar fusion procedure for fusing a calcaneus bone to a talus bone within a foot. However, the surgical steps described below could be implemented in other surgical procedures, including fracture procedures, for repairing abnormalities associated with other bones at other locations of the human musculoskeletal system.

Fewer or additional steps than are recited below could be performed within the scope of this disclosure. In addition, the recited order of steps depicted in FIGS. 9-12 is not intended to limit this disclosure.

Figures 9, 10:
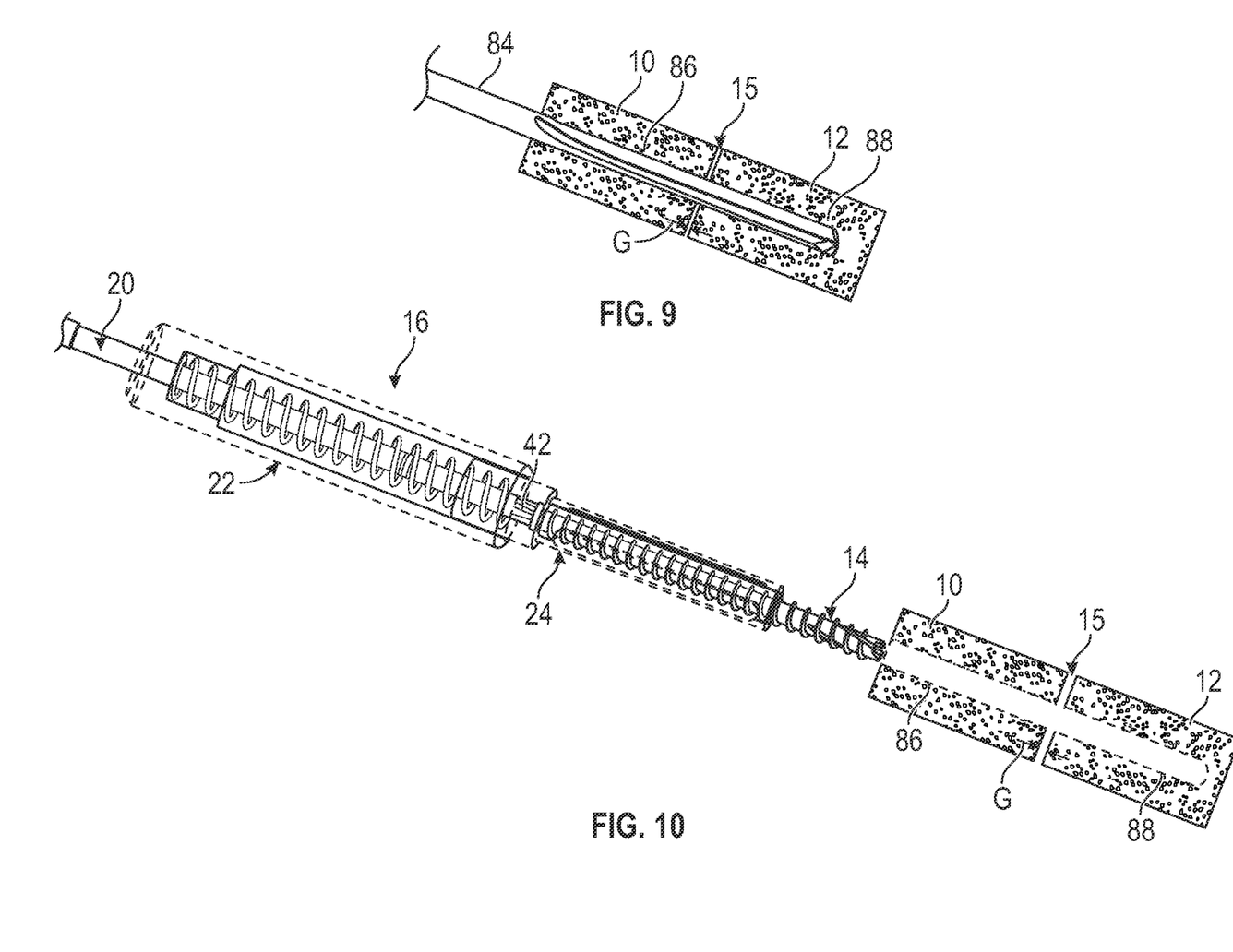
FIGS. 9, 10, 11, and 12 schematically illustrate an exemplary surgical method for performing an arthrodesis procedure or a fracture procedure.

Referring first to FIG. 9, a drill bit 84 may be used to prepare a first pilot hole 86 in the first bone segment 10 and a second pilot hole 88 in the second bone segment 12. The drill bit 84 may be drilled through the first bone segment 10, across the gap G that extends between the first and second bone segments 10, 12, and then at least partially through the second bone segment 12. In general, the gap G is located at the fracture line/arthrodesis site 15 between the first and second bone segments 10, 12. It may be desirable to reduce the gap G in order to achieve optimal fusion and healing at the fracture line/arthrodesis site 15.

Next, as schematically shown in FIG. 10, the engagement feature 42 of the drive shaft 20 of the compression/reduction driver 16 may be inserted into the corresponding engagement feature of the fixation device 14. The fixation device 14 may then approximated to the inlet of the first pilot hole 86. The compression/reduction driver 16 is shown in the relaxed position in FIG. 10.

Figure 11:
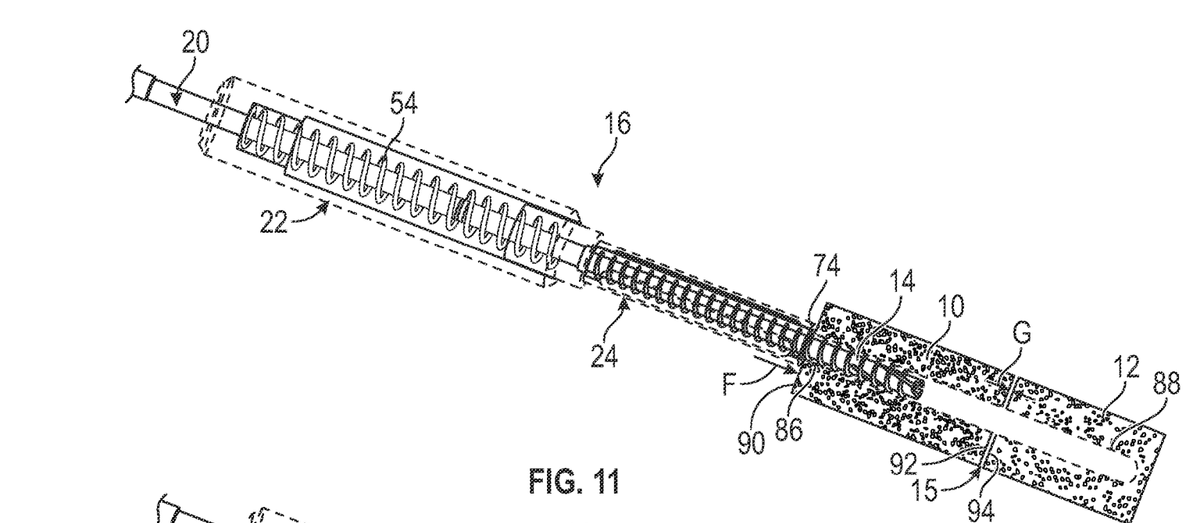

Referring next to FIG. 11, the surgeon may begin advancing the fixation device 14 into the first pilot hole 86 using the compression/reduction driver 16. The compression/reduction driver 16 is shown in a partially retracted position in FIG. 11. The fixation device 14 may be advanced into the first bone segment 10 by turning the handle 18 of the compression/reduction driver 16. Turning the handle 18 turns the drive shaft 20, thereby applying a rotational driving force to the fixation device 14. Simultaneously, a distal force applied to the handle 18 of the compression/reduction driver 16 forces the bone engaging surface 74 of the compression sleeve 24 into direct engagement with an exterior surface 90 of the first bone segment 10 via a spring force imparted by the spring 54. A force F is thereby imparted onto the first bone segment 10, and a reduction of the gap G at the fracture line/arthrodesis site 15 can thus be achieved prior to the fixation device 14 having reached the second pilot hole 88 of the second bone segment 12. Reduction of the gap G results in a first surface 92 of the first bone segment 10 being positioned into abutting contact with a second surface 94 of the second bone segment 12 before the fixation device 14 engages the second bone segment 12. The force F that is imparted onto the first bone segment 10 is transmitted from the user, to the spring retaining sleeve 22, and then to the compression sleeve 24, and therefore the force F may be imparted onto the first bone segment 10 independently of the rotational driving force that is applied to the fixation device 14 by the drive shaft 20.

Figure 12:
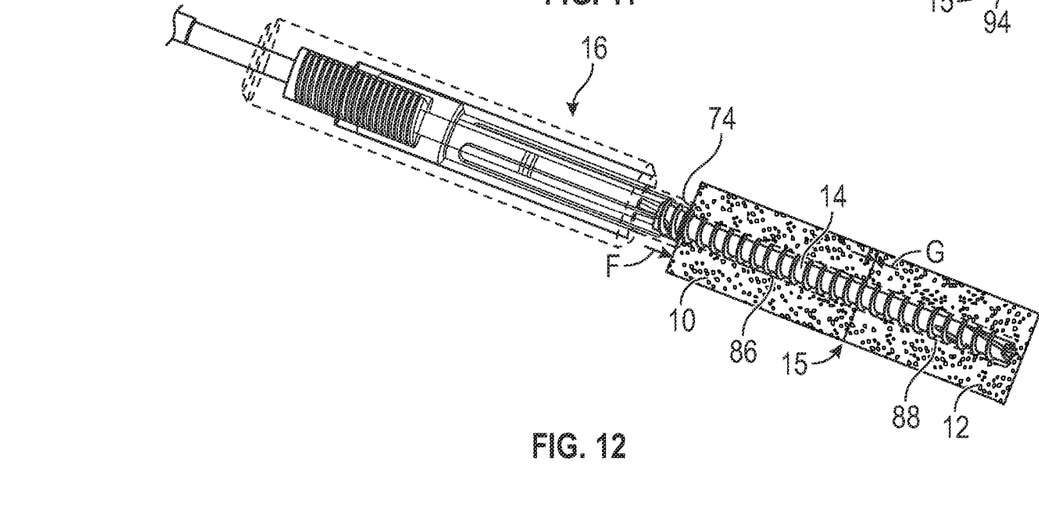

Referring to FIG. 12, the surgeon may continue advancing the fixation device 14 through the first bone segment 10, across the gap G, and then into the second pilot hole 88 by continuing to circumferentially rotate the handle 18 of the compression/reduction driver 16. The Force F may be maintained on the first bone segment 10 during this advancement to provide reduction assistance until the fixation device 14 engages the second pilot hole 88. The compression/reduction driver 16 is shown in a fully retracted position in FIG. 12. Once the fixation device 14 engages the second bone segment 12, reduction is maintained and compression is applied across the bone segments 10, 12 via a compressive screwing action. Once full reduction is achieved, the compression/reduction driver 16 may be disengaged from the fixation device 14.

The compression/reduction drivers of this disclosure aid in the reduction of bones at an arthrodesis site or fracture line during the implantation of a surgical fixation device. Unlike prior drivers, the compression/reduction drivers described herein are capable of simultaneously and independently providing reduction assistance across a gap between bone segments and driving a fixation device into the bone segments, thereby simplifying gap reduction during arthrodesis and fracture procedures.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A compression/reduction driver, comprising:
   a handle;
   a drive shaft secured to the handle and configured to engage a surgical fixation device,
   wherein the handle is rotatable relative to the drive shaft and is configured to apply a rotational driving force to the drive shaft;
   a spring retaining sleeve secured to the drive shaft;
   a compression sleeve movably secured relative to the spring retaining sleeve; and
   a spring extending between a first bearing surface of the spring retaining sleeve and a second bearing surface of the compression sleeve,
   wherein the spring is configured to apply a biasing force to bias the compression sleeve distally in a direction away from the spring retaining sleeve,
   wherein the spring retaining sleeve includes a first slot through which the spring and the drive shaft are visible, and the compression sleeve includes a second slot through which the drive shaft and the surgical fixation device are visible,
wherein the compression/reduction driver is configured such that, when the handle is rotated to apply the rotational driving force, the drive shaft, the spring retaining sleeve, and the compression sleeve rotate in unison.

2. The compression/reduction driver as recited in claim 1, wherein the handle is a ratcheting handle that includes a gripping portion and a toggle that is rotatable relative to the gripping portion to control a direction of the rotational driving force.

3. The compression/reduction driver as recited in claim 1, wherein the handle includes a release button depressible for releasing the drive shaft from the handle.

4. The compression/reduction driver as recited in claim 1, wherein the surgical fixation device is a headless compression screw, and further wherein the drive shaft includes a hexalobular or star-shaped driver tip configured to engage the headless compression screw.

5. The compression/reduction driver as recited in claim 1, wherein a length of the drive shaft that extends into the compression sleeve is adjustable.

6. The compression/reduction driver as recited in claim 5, wherein the spring retaining sleeve includes an internal thread that engages a threaded portion of the drive shaft for adjusting the length of the drive shaft that extends into the compression sleeve.

7. The compression/reduction driver as recited in claim 1, wherein a distal end portion of the compression sleeve includes a bone engaging surface.

8. The compression/reduction driver as recited in claim 7, wherein the bone engaging surface includes a plurality of bone engaging teeth at a serrated surface.

9. The compression/reduction driver as recited in claim 8, wherein the bone engaging surface establishes a distal most end of the compression/reduction driver.

10. The compression/reduction driver as recited in claim 1, comprising a pair of fixation device gripping legs operably coupled to the spring or the drive shaft.

11. The compression/reduction driver as recited in claim 1, wherein the spring retaining sleeve is fixed from movement relative to the compression sleeve.

12. The compression/reduction driver as recited in claim 1, wherein the compression/reduction driver is configured to impart a distal force that is independent of the rotational driving force, wherein the distal force is transmitted from the handle, to the spring retaining sleeve, and then to the compression sleeve, and wherein the compression/reduction driver is configured to impart the distal force and the rotational driving force simultaneously.

13. The compression/reduction driver as recited in claim 1, wherein an entire length of the handle extends along a first longitudinal axis that is collinear to a second longitudinal axis of the drive shaft.

14. The compression/reduction driver as recited in claim 1, wherein the spring is received directly around the drive shaft within the spring retaining sleeve.

15. A compression/reduction driver, comprising:
a handle;
a drive shaft secured to the handle and configured to engage a surgical fixation device,
wherein the handle is rotatable relative to the drive shaft and is configured to apply a rotational driving force to the drive shaft;
a spring retaining sleeve secured to the drive shaft;
a compression sleeve movably secured relative to the spring retaining sleeve; and
a spring extending between a first bearing surface of the spring retaining sleeve and a second bearing surface of the compression sleeve,
wherein the spring is configured to apply a biasing force to bias the compression sleeve distally in a direction away from the spring retaining sleeve,
wherein the spring retaining sleeve includes a first slot through which the spring and the drive shaft are visible, and the compression sleeve includes a second slot through which the drive shaft and the surgical fixation device are visible,
wherein the spring retaining sleeve is secured to the drive shaft by a weld or a bonding agent.

16. A compression/reduction driver, comprising:
a handle;
a drive shaft secured to the handle,
wherein the handle is rotatable relative to the drive shaft and is configured to apply a rotational driving force to the drive shaft;
a spring retaining sleeve secured to the drive shaft;
a compression sleeve movably secured relative to the spring retaining sleeve; and
a spring extending between a first bearing surface of the spring retaining sleeve and a second bearing surface of the compression sleeve,
wherein the spring is configured to apply a biasing force to bias the compression sleeve distally in a direction away from the spring retaining sleeve,
wherein the compression sleeve is movably secured to the spring retaining sleeve by a bayonet mount,
wherein the compression sleeve includes a tapered cylindrical body that includes a proximal end portion having a first diameter and a distal end portion having a second diameter that is smaller than the first diameter.

17. The compression/reduction driver as recited in claim 16, wherein the bayonet mount includes a pin on the compression sleeve and an L-shaped slot on the spring retaining sleeve.

18. A compression/reduction driver, comprising:
a handle;
a drive shaft secured to the handle and including a distal engagement portion configured to engage a surgical fixation device,
wherein the handle is rotatable relative to the drive shaft and is configured to simultaneously apply a rotational driving force and a distal force to the drive shaft;
a spring retaining sleeve secured to the drive shaft;
a compression sleeve movably secured relative to the spring retaining sleeve; and
a spring extending between a first bearing surface of the spring retaining sleeve and a second bearing surface of the compression sleeve,
wherein the spring is configured to apply a biasing force to bias the compression sleeve distally in a direction away from the spring retaining sleeve,
wherein, in a relaxed state of the compression/reduction driver, the distal engagement portion of the drive shaft extends a distance into the compression sleeve that is less than 50% of an overall length of the compression sleeve,
wherein the rotational driving force is configured to screw the surgical fixation device into a bone, and the distal force is configured to force the compression sleeve into engagement with an exterior surface of the bone, wherein the compression/reduction driver is configured such that, when the handle is rotated to apply the rotational driving force, the drive shaft, the spring retaining sleeve, and the compression sleeve rotate in unison.

19. The compression/reduction driver as recited in claim 18, wherein in a relaxed state of the compression/reduction driver, the distal engagement portion of the drive shaft extends a distance into the compression sleeve that is less than 25% of the overall length of the compression sleeve.

* * * * *